(12) United States Patent
Todd et al.

(10) Patent No.: US 8,538,710 B2
(45) Date of Patent: Sep. 17, 2013

(54) METHODS AND SYSTEMS FOR MONITORING LIFT USAGE

(75) Inventors: James D. Todd, Garnett, KS (US); Thomas Hollinger, Overland Park, KS (US); Christopher F. Fangrow, Harrisonville, MO (US)

(73) Assignee: Intellicare Network, LLC, Paola, KS (US)

(*) Notice: Subject to any disclaimer, the term of this patent is extended or adjusted under 35 U.S.C. 154(b) by 463 days.

(21) Appl. No.: 12/794,438

(22) Filed: Jun. 4, 2010

(65) Prior Publication Data

US 2011/0082655 A1 Apr. 7, 2011

Related U.S. Application Data

(60) Provisional application No. 61/184,642, filed on Jun. 5, 2009.

(51) Int. Cl.
*G01R 31/36* (2006.01)
(52) U.S. Cl.
USPC .......................................................... 702/63
(58) Field of Classification Search
USPC .............................................. 702/63; 5/600
See application file for complete search history.

(56) References Cited

U.S. PATENT DOCUMENTS

| | | | |
|---|---|---|---|
| 2006/0150332 A1* | 7/2006 | Weismiller et al. | 5/600 |
| 2006/0279427 A1* | 12/2006 | Becker et al. | 340/573.4 |
| 2008/0201851 A1* | 8/2008 | Menkedick et al. | 5/611 |
| 2009/0094746 A1 | 4/2009 | Ferraresi | |
| 2009/0102667 A1* | 4/2009 | Rees | 340/573.1 |

OTHER PUBLICATIONS

International Search Report and Written Opinion for PCT/US2010/037471 dated Jul. 30, 2010 (13 pages).

* cited by examiner

*Primary Examiner* — Tung S Lau
*Assistant Examiner* — Xiuquin Sun
(74) *Attorney, Agent, or Firm* — Polsinelli PC

(57) ABSTRACT

Methods and systems for lift monitoring are described. In one embodiment, a first operation signal may be received from a first relay coupled to an electro-mechanical patient lift when the electro-mechanical patient lift is being operated in a first position. A second operation signal may be received from a second relay coupled to the electro-mechanical patient lift when the electro-mechanical patient lift is being operated in a second position. A determination of whether a lift qualification threshold is met may be based on the receiving of the first operation signal and the second operation signal. An occurrence of a lift may be recorded when a determination is made that the lift qualification threshold is met. Additional methods and systems are disclosed.

16 Claims, 19 Drawing Sheets

METHODS AND SYSTEMS FOR MONITORING LIFT USAGE

CROSS-REFERENCE TO A RELATED APPLICATION

This application claims the benefit of United States Provisional patent application entitled "Methods and Systems for Monitoring Lift Usage", Ser. No. 61/184,642, filed 5 Jun. 2009, the entire contents of which are herein incorporated by reference.

FIELD

This application relates to methods and systems for device monitoring, and more specifically to methods and systems for monitoring usage of electro-mechanical lifts.

BACKGROUND

Healthcare facilities have had a tremendous amount of back injuries and workmen compensation claims, a majority of which were caused by staff manually lifting and repositioning patients that have at least some difficulty. Patients at times were also injured by not being lifted or repositioned properly.

Today, most healthcare facilities have purchased electro-mechanical lift equipment to help with the lifting and repositioning of patients. The purchase of lifts did not automatically reduce injuries at the rate the facilities had hoped. Some staff still continue to perform lifts or repositioning without use of the lift equipment.

DETAILED DESCRIPTION

Example methods and systems for lift monitoring are described. In the following description, for purposes of explanation, numerous specific details are set forth in order to provide a thorough understanding of example embodiments. It will be evident, however, to one of ordinary skill in the art that embodiments of the invention may be practiced without these specific details.

In an example embodiment, one or more measurement devices are coupled to an electro-mechanical patient lift. The measurement devices may make one or more readings of the electro-mechanical patient lift. The readings may be provided to a transmitter. The transmitter may then provided the readings to a monitoring computing device, or may itself determine whether a lift has occurred based on analysis of the readings. Once the determination of whether a lift has occurred has been made, the resulting data may be stored and used in a variety of ways.

In some embodiments, the methods and systems for lift monitoring passively provide real-time information regarding use of the lifting equipment directly to administrators of facilities that have electro-mechanical patient lifts. In some embodiments, the use of the methods and systems for lift monitoring may encourage greater usage of the electro-mechanical patient lifts by equipment operators at these facilities. In some embodiments, the use of the methods and systems for lift monitoring may reduce injuries caused by non-use or improper use of electro-mechanical patient lifts by certain operators at these facilities that are not using the electro-mechanical patient lifts as directed by an administrator.

In some embodiments, the methods and systems may be used to incrementally train staff in a facility to use electro-mechanical patient lifts for one of a variety of different lift types. These methods and systems may provide program management and increase cultural change acceptance of greater use of electro-mechanical patient lifts at facilities.

In some embodiments, the methods and systems may be used to reduce the number of injuries relating to unassisted lifts. In addition, the methods and systems may enable continued and greater adoption of electro-mechanical patient lifts for a variety of different lifting activities that are often performed in facilities.

In some embodiments, the methods and systems may be used to keep the correct number of slings and accessories in the unit or department of the facility. This information may be used to reduce facility costs in lost slings and improve outcomes (e.g., based on a better chance the correct slings in the correct number will be in the unit or department when needed).

In some embodiments, the methods and systems enable analysis of lift data and then based on that analysis distribute usable data to certain staff based on what the data is and the values of that data. The methods and systems may then be used to provide recommendations for improved methods of dealing with a subpar outcome.

Figure 1:
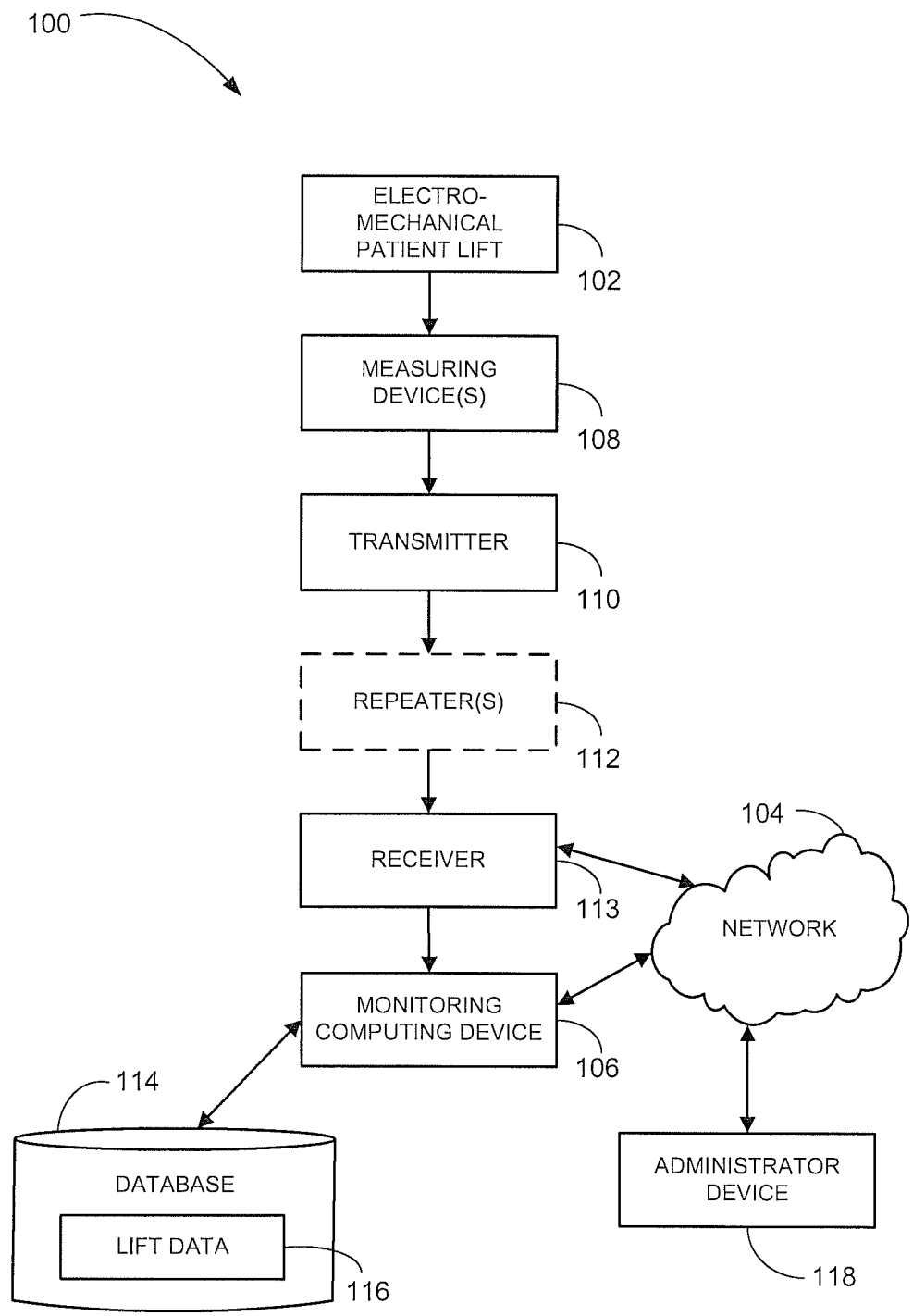
FIG. 1 is a block diagram of an example lift monitoring system, according to an example embodiment.

FIG. 1 is a block diagram of an example lift monitoring system 100, according to an example embodiment. The lift monitoring system 100 includes an electro-mechanical patient lift 102 that is used in a hospital or other health care facility to assist in the lifting or repositioning of a patient. The electro-mechanical patient lift 102 may be a portable or nonportable lift. The nonportable lift is usually affixed in a patient room of the facility that is designated for use by certain patients that need lift or repositioning assistance. The portable lifts are movable from room to room in the facility. The portable lifts may include a total care lift and/or a stand assist lift.

Data regarding use of the electro-mechanical patient lift 102 is obtained by use of one or more measuring devices 108. The measuring devices 108 make readings during operation or non-operation of the electro-mechanical patient lift 102.

The readings may be used to determine whether a patient lift using the electro-mechanical patient lift 102 was performed. The measuring devices 108 may be attached to, integrated with, or otherwise coupled to the electro-mechanical patient lift 102. Examples of the measuring devices 108 include relays, current sensors, load sensors, vibration sensors, motion sensors, or the like. Other types of measuring devices may also be used alone or in combination.

The measuring devices 108 provide the readings to a transmitter 110. In some embodiments, the transmitter 110 provides the readings to a receiver 113. In other embodiments, the transmitter 110 receives the readings and determines whether a lift or a non-lift has occurred. The determination of whether the lift or non-lift has occurred may then be stored on the transmitter 110 for later reading by an administrator of the facility in which the system 100 is deployed. The determination may, in some embodiments, be communicated to a monitoring computing device 106.

The transmitter 110 may be attached to, integrated with, or otherwise coupled to the electro-mechanical patient lift 102. The transmitter 110 may be separate from or integrated with one or more of the measuring devices 108. The transmitter 110 may communicate through a wired or wireless medium. For example, the transmitter 110 may send information in a facility at a certain frequency. An example of the transmitter 110 is the INOVONICS EE1212 dual input universal transmitter by Inovonics Wireless Corporation. However, other types of transmitters with a differing number of inputs may also be used.

In some embodiments, one or more repeaters 112 are used with the system 100 to provide the readings and/or other information from the transmitter 110 to a receiver 113. An example of the repeater 112 is the INOVONICS EN5040 by Inovonics Wireless Corporation. However, other types of repeaters may also be used. Multiple repeaters 112 may be deployed in a facility to ensure that the receiver 113 ultimately receives the information.

In one embodiment, a repeater 112 may be coupled to a locator. The locator may add a location identifier to a received signal that may be used to identify the location of the transmitter 110.

In some embodiments, the receiver 113 receives readings made by the measuring devices 108 and/or results of determinations made by the transmitter 110, and provides the information to the monitoring computing device 106.

The receiver 113 is coupled to the monitoring computing device 106. For example, the receiver 113 may be a 9 pin serial receiver that is physically and electronically connected to the monitoring computing device 106 through a serial card. In one particular embodiment, the receiver 113 is the INOVONICS EN6040 by Inovonics Wireless Corporation. In some embodiments, the monitoring computing device 106 is located inside the facility in which the electro-mechanical patient lifts 102 are located. In other embodiments, the monitoring computing device 106 is located outside the facility (e.g., a separate monitoring center or as a remote server).

The transmitter 110 and/or the receiver 113 may include a counter to record a number of lifts that have been performed by the electro-mechanical patient lift 102. In some embodiments, the number indicated by the counter may be read by an administrator and reset without providing the number of lifts to the monitoring computing device 106. In other embodiments, the number indicated by the counter is provided to the monitoring computing device 106.

The monitoring computing device 106 may store the readings and/or determinations as lift data 116 from a number of electro-mechanical patient lifts 102 (e.g., of a facility) in a database 114. The monitoring computing device 106 may receive readings and determine whether a lift or non-lift has occurred. The monitoring computing device 106 may receive a count on a number of lifts and/or non-lifts performed by the electro-mechanical patient lift 102. The results of the determination and/or the counts may be stored as the lift data 116.

Examples of the monitoring computing device 106 include a set-top box, a gaming unit, a receiver card, a set-top box (STB) a mobile phone, a personal digital assistant (PDA), a display device, a generic computing system, or the like. Other devices may also be used.

The monitoring computing device 106 may use the lift data 116 to generate one or more report message (e.g., regarding lifts that have been performed in a certain geographic area). In one embodiment, the monitoring computing device 106 may archive the lift data 116 for later reporting.

An administrator device 118 may receive some or all of these report messages from the monitoring computing device 106. The administrator device 118 may be a computing device, pager, cell phone, or other electronic device operated by an administrator to obtain information regarding the operation of the system 100. For example, the administrator may use the report messages received to determine that certain electro-mechanical patient lifts 102 are not being used or not being used properly. In one embodiment, the administrator may receive the report messages real time in an email.

The administrator is a person that may use information about operation of the lifts that occurred in a facility (or multiple facilities). For example, the administrator may be a single person in charge of a facility or the operations of some portion of the facility. Multiple administrators may include staff personnel of a facility that may receive the same information or different information depending on particular settings of the monitoring computing device 106. Other examples of administrators include unit managers, department managers, risk managers, or the like.

The report messages may be transmitted over a network 104 from the computer monitoring device 106 to the administrator device 118. Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Other conventional and/or later developed wired and wireless networks may also be used.

By way of an example, an administrator may log into the monitoring computing device 106 during a shift change, identify the patients that need lift assistance (and their associated rooms), and determine whether lift assistance was provided to these patients using the electro-mechanical patient lifts 102. The administrator may ignore rooms and/or patients that are not in need of lift assistance.

Figure 2:
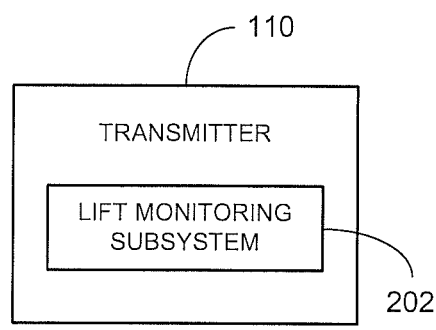
FIG. 2 illustrates an example transmitter that may be deployed in the lift monitoring system of FIG. 1, according to an example embodiment.

FIG. 2 illustrates an example transmitter 110, according to an example embodiment. The transmitter 110 is shown to include a lift monitoring subsystem 202. The lift monitoring subsystem 202 receives readings from the measuring devices 108 and determines whether a patient lift has occurred. The transmitter 110 with the lift monitoring subsystem 202 may be deployed in the system 100, or may be deployed in another system.

Figure 3:
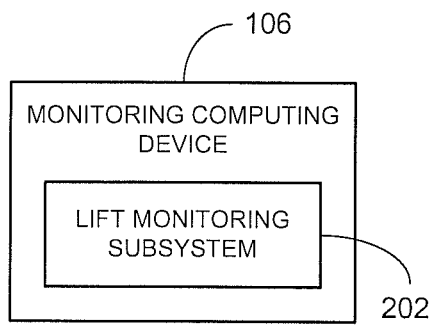
FIG. 3 illustrates an example monitoring computing device that may be deployed in the lift monitoring system of FIG. 1, according to an example embodiment.

FIG. 3 illustrates an example monitoring computing device 106, according to an example embodiment. The monitoring computing device 106 is shown to include a lift monitoring subsystem 202. The monitoring computing device 106 with the lift monitoring subsystem 202 may be deployed in the system 100, or may be deployed in another system.

In some embodiments, the lift monitoring subsystem 202 may be included in both the transmitter 110 and the monitoring computing device 106, while in other embodiments, the lift monitoring subsystem 202 is included in only one of the devices. In yet another embodiment, a portion of the lift monitoring subsystem 202 is included in the transmitter 110 and a remaining portion is included in the monitoring computing device 106. Other configurations may also be used.

Figure 4:
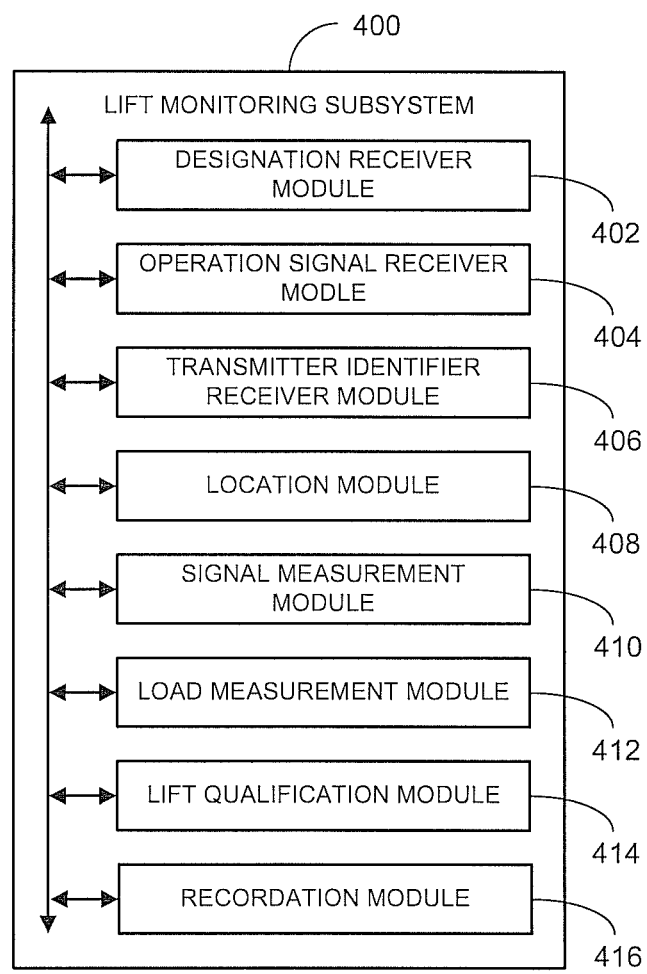
FIGS. 4 and 5 are block diagrams of example lift monitoring subsystems that may be deployed within the transmitter of FIG. 2 and/or the monitoring computing device of FIG. 3, according to example embodiments.

FIG. 4 illustrates an example lift monitoring subsystem 400 that may be deployed as the lift monitoring subsystem 202 in the monitoring computing device 106, the transmitter 110, or otherwise deployed in another system. One or more modules are communicatively coupled and included in the lift monitoring subsystem 400 to enable monitoring of the electro-mechanical patient lift 102. The modules of the lift monitoring subsystem 400 that may be included are a designation receiver module 402, an operation signal receiver module 404, a transmitter identifier receiver module 406, a location module 408, a signal measurement module 410, a load measurement module 412, a lift qualification module 414, and a recordation module 416. Other modules may also be included. In some embodiments, the modules of the lift monitoring subsystem 400 may be distributed so that some of the modules are deployed in the monitoring computing device 106 and others are deployed in the transmitter 110. In one particular embodiment, the lift monitoring subsystem 400 includes a processor, memory coupled to the processor, and a number of the aforementioned modules deployed in the memory and executed by the processor.

In some embodiments, the designation receiver module 402 receives a threshold designation. The threshold designation is typically received by an administration of the facility and designates certain time thresholds that are enforced in order to qualify a certain activity using the electro-mechanical patient lift 102 as a lift. The threshold designation may include an up time threshold, a down time threshold, and/or a delay time ceiling. The up time threshold indicates an amount of time that the electro-mechanical patient lift 102 is operated in an up position. The down time threshold indicates an amount of time that the electro-mechanical patient lift 102 is operated in a down position. The delay time ceiling indicates a maximum amount of time between the operation of the electro-mechanical patient lift 102 in the up position and the operation of the electro-mechanical patient lift 102 in the down position. Other thresholds may also be designated.

When the electro-mechanical patient lift is being operated in a first position (e.g., an up position), the operation signal receiver module 404 receives a first operation signal from a first relay. Relays are a type of measuring device 108 that may be used with the system 100. The operation signal receiver module 404 also receives a second operation signal from a second relay when the electro-mechanical patient lift 102 is being operated in a second position (e.g., a down position).

In some embodiments, the transmitter identifier receiver module 406 receives a transmitter identifier when the electro-mechanical patient lift 102 is being operated. The transmitter identifier may be provided with the operation signals, or may be separately provided. For example, the transmitted identifier may be provided simultaneously with the operation signals, before the operation signals are provided, or after the operation signals were provided. In other embodiments wherein the electro-mechanical patient lift 102 is an overhead patient lift, the electro-mechanical patient lift 102 may be hardwired to the monitoring computing device 106. The monitoring computing device 106 may then identify the particular electro-mechanical patient lift 102 based on exact knowledge of which of many electro-mechanical patient lifts 102 of a facility that provided a reading.

In some embodiments, the location module 408 is deployed in the lift monitoring subsystem 400 to identify a location associated with the transmitter identifier and/or receive positional data associated with a location of the electro-mechanical patient lift 102. The positional data may be received from a Global Positioning System (GPS) receiver, a tag associated with the electro-mechanical patient lift 102, a tag associated with an operator using the electro-mechanical patient lift 102, or the like.

When included in the example lift monitoring subsystem 400, the signal measurement module 410 measures signal duration of the operation signals to identify how long the electro-mechanical patient lift 102 is operated in the first position and the second position. In other embodiments, time between signal measurements is used.

In some embodiments, load measurement is received from a load sensor by the load measurement module 412 to determine whether the load measurement meets a load threshold. The load threshold is an amount of load on the electro-mechanical patient lift 102 that qualifies whether a lift has been made. Use of a load threshold may reduce the amount of non-lifts that are qualified as lifts. The designation of the load threshold may be received by the designation receiver module 402, or may be otherwise set.

The lift qualification module 414 determines whether a lift qualification threshold is met (e.g., based on receipt of operation signals). In one embodiment, the lift qualification threshold is one or more qualifications (e.g., amount, type and/or duration) of one or more signals to be received that are designated as being sufficient to qualify a reading as being a lift. For example, the lift qualification threshold may designate a reading as being a lift when the electro-mechanical patient lift 102 is operated in the up position for at least five seconds and operated in the down position for at least five seconds. The lift qualification may be hard-coded (e.g., by a manufacturer), or may be designated from time to time by an administrator of a facility or other person. In some embodiments, lift qualification module 414 determines whether the lift qualification threshold is met based on the operations signal and a determination that the load measurement meets the load threshold.

The recordation module 416 records an occurrence of a lift when a determination is made that the lift qualification threshold is met. In some embodiments, the recordation module 416 records the transmitter identifier with the occurrence of the lift. In other embodiments, the recordation module 416 records the location with the occurrence of the lift. In some embodiments, the recordation module 416 records an occurrence of a non-lift when a determination is made that the lift qualification threshold is not met. The recordation of the lifts may be made as the lift data 116 in the database 114 (see FIG. 1).

Figure 5:
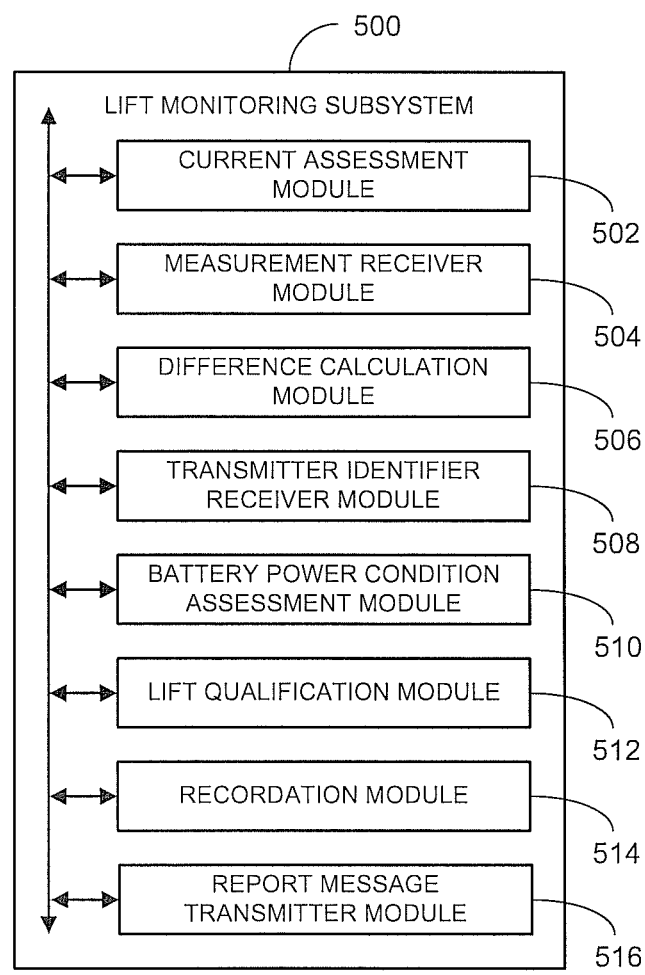

FIG. 5 illustrates an example lift monitoring subsystem 500 that may be deployed as the lift monitoring subsystem 202 in the monitoring computing device 106, the transmitter 110, or otherwise deployed in another system. One or more modules are communicatively coupled and are included in the lift monitoring subsystem 500 to enable monitoring of the electro-mechanical patient lift 102. The modules of the lift monitoring subsystem 500 that may be included are a current assessment module 502, a measurement receiver module 504, a difference calculation module 506, a transmitter identifier receiver module 508, a battery power condition assessment module 510, a lift qualification module 512, a recordation module 514, a report message transmitter module 516, and/or a compliance module 518. Other or different modules may also be included. In some embodiments, the modules of the lift monitoring subsystem 500 may be distributed so that some of the modules are deployed in the monitoring computing device 106 and others are deployed in the transmitter 110. In some embodiments, the modules of the lift monitoring subsystem 400 may be included with the modules of the lift monitoring subsystem 500, or the lift monitoring subsystem 500 may be included with the modules of the lift monitoring subsystem 400. In one particular embodiment, the lift monitoring subsystem 500 includes a processor, memory coupled to the processor, and a number of the aforementioned modules deployed in the memory and executed by the processor.

In general, the lift monitoring subsystem 500 uses a current sensor as the measuring device 108 instead of the relays used by the lift monitoring subsystem 400. The lift monitoring subsystem 500 may be used instead of or in addition to the lift monitoring subsystem 400. Other lift monitoring subsystems that include different measuring devices 108 may also be used.

In some embodiments, the current assessment module 502 accesses a non-usage current associated with the electro-mechanical patient lift 102. The non-usage current is an amount of current flowing through the electro-mechanical patient lift 102 when the electro-mechanical patient lift 102 is not in operation. In some embodiments, the designation receiver module 402 may receive the amount of the non-current usage.

The measurement receiver module 504 receives a measurement of current from a current sensor coupled to the electro-mechanical patient lift 102. The difference calculation module 506 calculates a current difference between the measurement of current and the non-usage current.

The transmitter identifier receiver module 508 receives a transmitter identifier from the transmitter 110 (see FIG. 1). The battery power condition assessment module 510 assesses a battery power condition of a lift battery used by the electro-mechanical patient lift 102. The battery power condition may be affected based on a current operation being performed by the electro-mechanical patient lift 102, past use of the electro-mechanical patient lift 102, age of the lift battery, or the like.

The lift qualification module 512 determines whether a lift qualification threshold is met. In some embodiments, the determination is made based on receipt of the measurement of current. In other embodiments, the determination is made based on the current difference meeting the lift qualification threshold. In some embodiments, the determination includes assessment of the battery power condition.

The recordation module 514 records an occurrence of a lift when a determination is made that the lift qualification threshold is met. In some embodiments, the transmitter identifier is recorded with the occurrence of the lift.

The report message transmitter module 516 transmits a report message to the administrator device 118. The report message may include information associated with the recording of the occurrence of the lift. The report message may include a lift usage confirmation of the electro-mechanical patient lift 102 and/or of an additional electro-mechanical patient lift, a lift nonuse notification of the electro-mechanical patient lift 102 and/or of an additional electro-mechanical patient lift, or the like.

In some embodiments, the report message transmitter module 516 is deployed in the lift monitoring subsystem 400. In some embodiments, the designation receiver module is deployed in the lift monitoring subsystem 500. Other variations on the inclusion and coupling of modules in the lift monitoring subsystems 400, 500 may be used.

Figure 6:
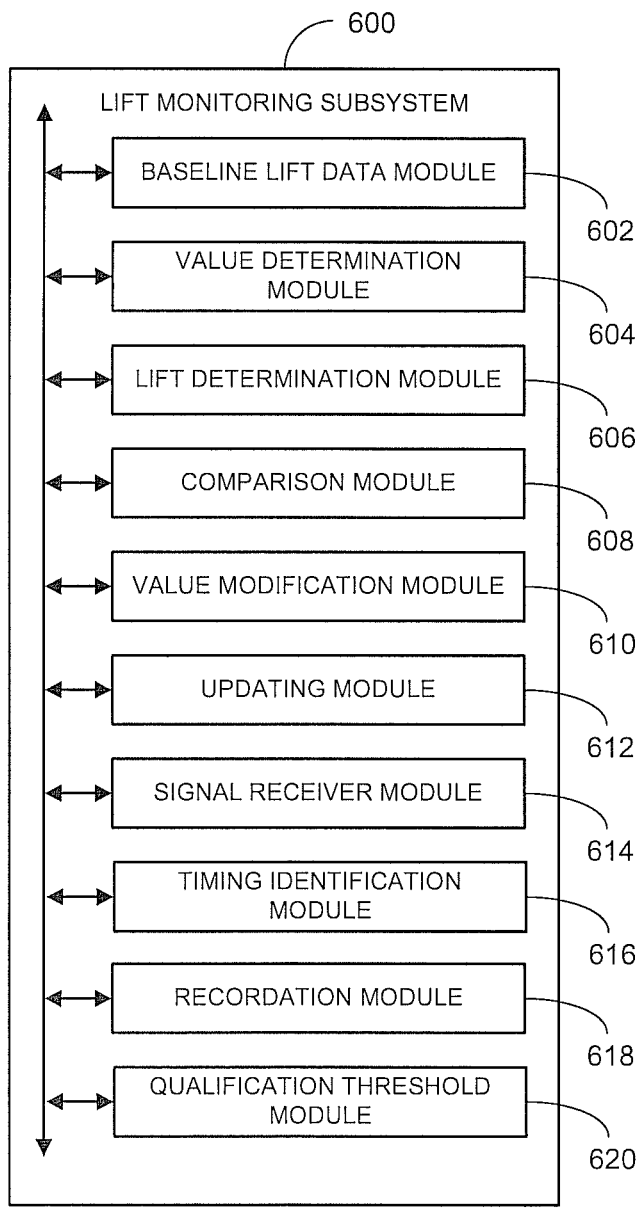
FIGS. 6-10 are block diagrams of flowcharts illustrating methods for lift monitoring, according to example embodiments.

FIG. 6 illustrates an example lift monitoring subsystem 600 that may be deployed as the lift monitoring subsystem 202 in the monitoring computing device 106, the transmitter 110, or otherwise deployed in another system. One or more modules are communicatively coupled and are included in the lift monitoring subsystem 600 to enable monitoring of the electro-mechanical patient lift 102. The modules of the lift monitoring subsystem 600 that may be included are a baseline lift data module 602, a value determination module 604, a lift determination module 606, a comparison module 608, a value modification module 610, an updating module 612, a signal receiver module 614, a timing identification module 616, a recordation module 618, and/or a qualification threshold module 620. Other or different modules may also be included. In some embodiments, the modules of the lift monitoring subsystem 600 may be distributed so that some of the modules are deployed in the monitoring computing device 106 and others are deployed in the transmitter 110. In some embodiments, the modules of the lift monitoring subsystem 400, 500 may be included with the modules of the lift monitoring subsystem 600, or the lift monitoring subsystem 600 may be included with the modules of the lift monitoring subsystems 400, 500. In one particular embodiment, the lift monitoring subsystem 600 includes a processor, memory coupled to the processor, and a number of the aforementioned modules deployed in the memory and executed by the processor.

In some embodiments, the baseline lift data module 602 accesses baseline lift data of a patient facility and the value determination module 604 determines a compliance value based on the baseline lift data.

The lift determination module 606 determines a number of patient lifts performed during a time period in an area of a patient facility.

The comparison module 608 compares the number of patient lifts performed to a compliance value.

The value modification module 610 modifies the compliance value based on a result of comparison between the number of patient lifts performed to the compliance value.

In some embodiments, the value modification 610 module receives a compliance adjustment from a user and modifies the compliance value based on the result of comparison between the number of patient lifts performed to the compliance value and receipt of the compliance adjustment.

The updating module 612 updates the baseline data based on the number of patient lifts performed during the time period.

The signal receiver module 614 receives signals from measuring devices coupled to an electro-mechanical patient lift.

The timing identification module 616 identifies lift usage timing based on receipt of a single signal or multiple signals.

The recordation module 618 records lift usage data based on receipt of the signal and identification of the lift usage timing.

In some embodiments, the qualification threshold module 620 determines whether a lift qualification threshold is met based on receipt of the signal and the identification of the lift usage timing and the recordation module 618 records an occurrence of a lift when a determination is made that the lift qualification threshold is met.

In some embodiments, the timing identification module 616 identifies total lift usage timing during a time period for electro-mechanical patient lifts based on lift usage data for the electro-mechanical patient lift and the comparison module 608 compares total lift usage timing to a compliance value.

Figure 7:
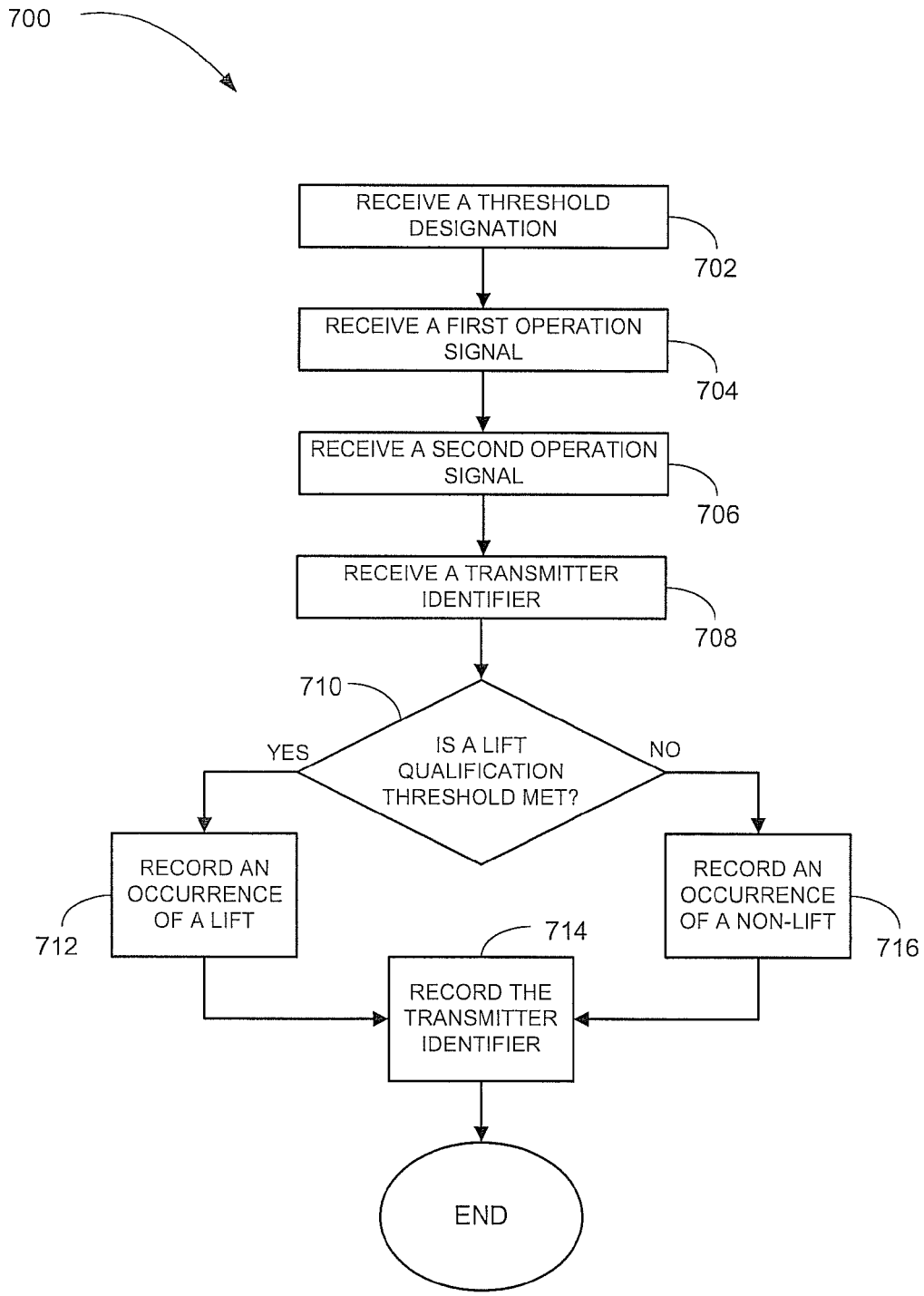

FIG. 7 illustrates a method 700 for lift monitoring according to an example embodiment. The method 700 may be performed by the monitoring computing device 106, the transmitter 110 of the system 100 (see FIG. 1), or may be otherwise performed.

A threshold designation may be received at block 702. The threshold designation may include an up time threshold, a down time threshold, and/or a delay time ceiling. The threshold may also include other designations.

At block 704, a first operation signal is received from a first relay coupled to the electro-mechanical patient lift 102 when the electro-mechanical patient lift 102 is being operated in a first position (e.g., an up position).

At block 706, a second operation signal is received from a second relay coupled to the electro-mechanical patient lift 102 when the electro-mechanical patient lift 102 is being operated in a second position (e.g., a down position).

In some embodiments, a transmitter identifier is received from the transmitter 110 at block 708 when the electro-mechanical patient lift 102 is being operated.

At decision block 710, a determination of whether a lift qualification threshold is met based on receipt of the first operation signal and the second operation signal. In some embodiments, the determination is based on receipt of the first operation signal, the second operation signal, and the designation of the up time threshold, the down time threshold, and/or the delay ceiling.

In some embodiments, a load measurement is received from a load sensor coupled to the electro-mechanical patient lift 102 and a determination of whether the load measurement meets a load threshold is made. The determination of whether the lift qualification threshold is met is then made at decision block 710 based on receipt of the first operation signal and the second operation signal and a determination that the load measurement meets the load threshold.

In some embodiments, a first signal duration of receiving the first operation signal is measured and a second signal duration of receiving the second operation signal is measured. The determination of whether the lift qualification threshold is met is then made at decision block 710 based on a determination of whether the first signal duration meets the up time threshold and a determination of whether the second signal duration meets the down time threshold.

If the determination is made that the lift qualification threshold is met, an occurrence of a lift is recorded at block 712. In some embodiments, the transmitter identifier is recorded at block 714 with the occurrence of the lift.

If a determination is made that the lift qualification threshold is not met at decision block 710, an occurrence of a non-lift is recorded at block 716. In some embodiments, the transmitter identifier is recorded at block 714 with the occurrence of the non-lift.

In some embodiments, a location associated with the transmitter identifier is identified and the location is recorded with the occurrence of the lift or non-lift. In other embodiments, positional data associated with a location of the electro-mechanical patient lift 102 is received and the location is recorded with the occurrence of the lift or non-lift.

Figure 8:
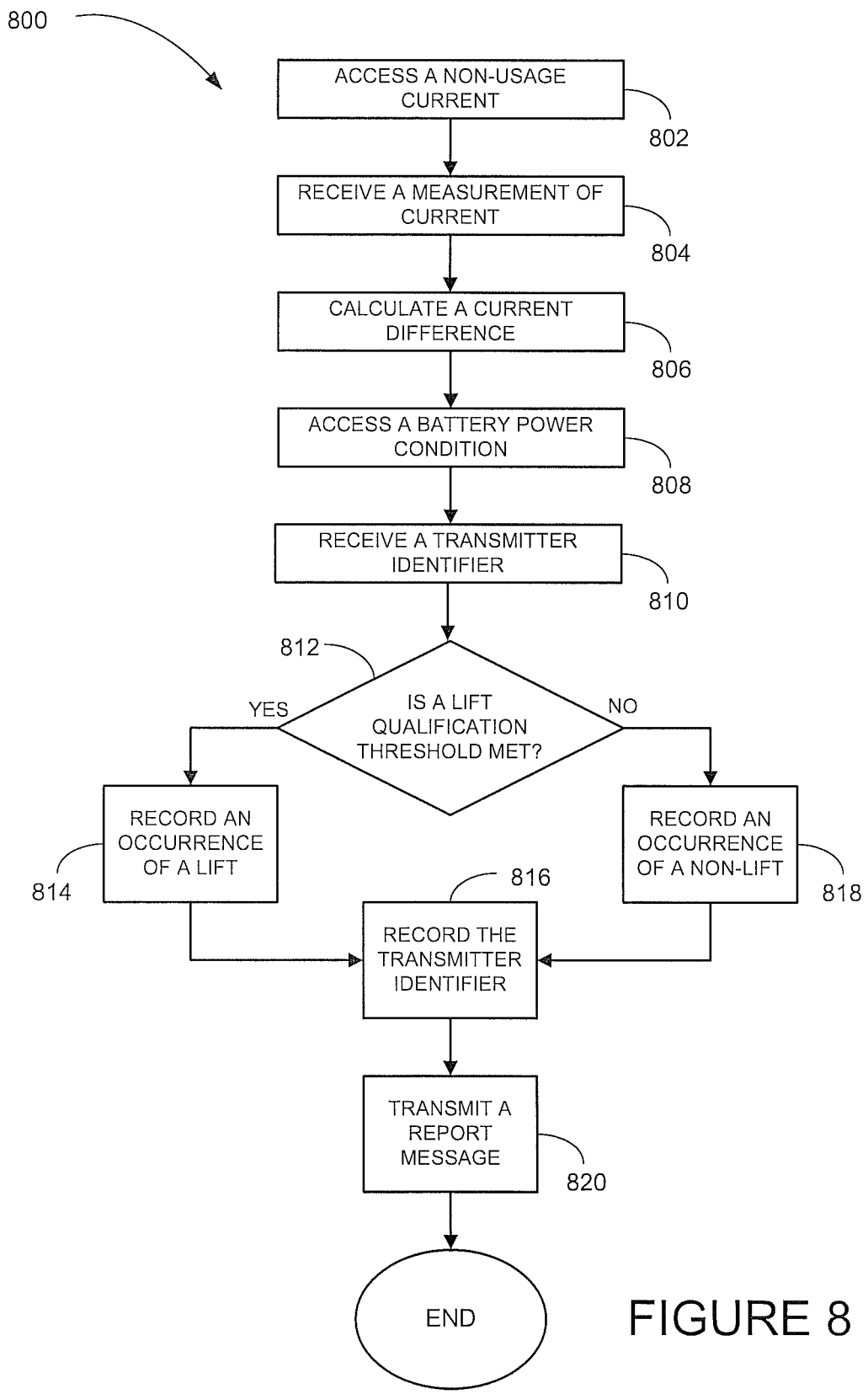

FIG. 8 illustrates a method 800 for lift monitoring according to an example embodiment. The method 800 may be performed by the monitoring computing device 106, the transmitter 110 of the system 100 (see FIG. 1), or may be otherwise performed.

A non-usage current associated with the electro-mechanical patient lift 102 is accessed at block 802. A measurement of current from a current sensor coupled to the electro-mechanical patient lift 102 is received at block 804.

A calculation of a current difference between the measurement of current and the non-usage current is made at block 806. In some embodiments, a transmitter identifier is received from the transmitter 110 at block 808.

A battery power condition of a lift battery of the electro-mechanical patient lift 102 may be accessed at block 810.

At decision block 812, a determination of whether a lift qualification threshold is met based on receipt of the measurement of current is made. The determination of the whether the lift qualification threshold is met may be based on the current difference meeting the lift qualification threshold. In some embodiments, the determination of whether the lift qualification threshold is met is based on receipt of the measurement of current change and assessment of the battery power condition.

In an example embodiment, a threshold designation may be received prior to the operations performed at decision block 812. The threshold designation may include a certain battery condition and/or a specified amount of current difference that may be used to determine whether lift qualification threshold. The threshold may also include other designations.

If the determination is made that the lift qualification threshold is met, an occurrence of a lift is recorded at block 814. In some embodiments, the transmitter identifier is recorded at block 816 with the occurrence of the lift.

If a determination is made that the lift qualification threshold is not met at decision block 812, an occurrence of a non-lift is recorded at block 818. The transmitter identifier may be recorded at block 816 with the occurrence of the non-lift. In some embodiments, the report message regarding the occurrences of lifts and non-lifts is transmitted to an administrator through the administrator device 118 (see FIG. 1) at block 820.

In an example embodiment, the report message transmitted at block 820 may also be transmitted after the completions of the operations at block 712, block 714, and/or block 716 (see FIG. 7).

The report message may be transmitted hourly, daily, weekly, monthly, quarterly, or at some other time increment. The report message may include information regarding all occurrences of lifts and/or non-lifts, or a subset of the number of occurrences. For example, only the occurrences of lifts on particular electro-mechanical patient lifts 102 in a particular facility may be reported. The information provided in the report message may include aggregate information regarding the lifts and/or non-lifts, or more detailed information may be provided. For example, certain electro-mechanical patient lifts 102 may be identified in the report message, or the report message may include aggregated information about a certain number or grouping of electro-mechanical patient lifts 102.

By way of an example, if there are twelve rooms in a particular ward of a facility and four of those rooms have patients that need lift assistance, the report message may be sent to the department manager's phone at the end of the shift confirming the electro-mechanical patient lifts 102 were used in those rooms and how many lifts/transfers were performed. The department manager may be provided with crucial information on nonuse of certain of the electro-mechanical patient lifts 102 so that the manager may immediately communicate with staff and immediately rectify the problem. That same information may also be sent to a risk manager that may have the ultimate responsibility for the whole facility. If, as an example, the risk manager sees from the information that three of the twelve departments are not utilizing the potential of their lift equipment properly, automatically notifications of the noncompliance may be sent to immediately let the department managers know that this occurred and to timely rectify the problem.

Figure 9:
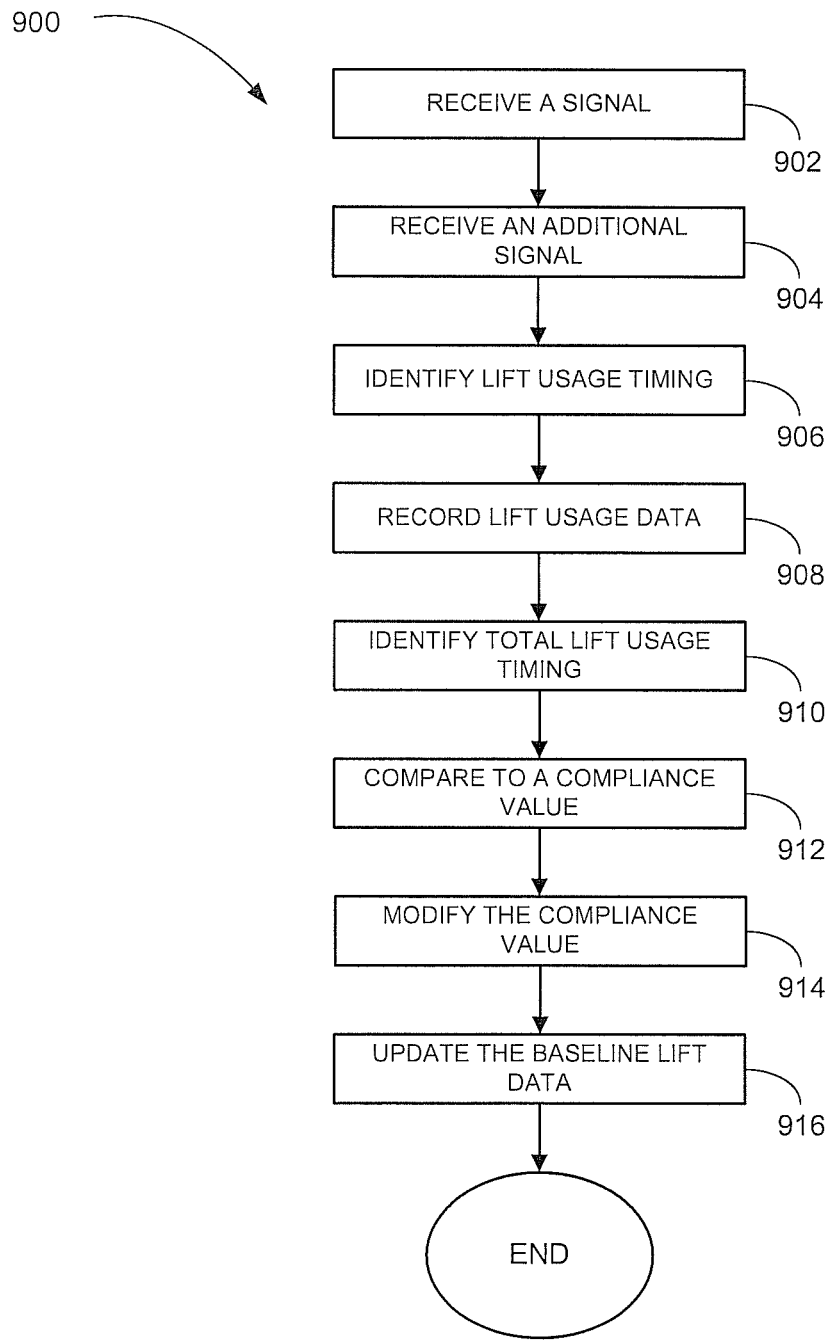

FIG. 9 illustrates a method 900 for lift monitoring according to an example embodiment. The method 900 may be performed by the monitoring computing device 106, the transmitter 110 of the system 100 (see FIG. 1), or may be otherwise performed.

A signal is received from a measuring device coupled to an electro-mechanical patient lift at block 902.

An additional signal may be received at block 904. In some embodiments, the additional signal is received from the measuring device at a different time than the signal. In some embodiments, the additional signal is received from an additional measuring device coupled to the electro-mechanical patient lift at a different time than the signal.

Lift usage timing is identified at block 906 based on receipt of the signal. In some embodiments, identification of the lift usage timing may be based on receipt of the signal and the additional signal.

Lift usage data is recorded at block 908 based on receipt of the signal and identification of the lift usage timing. In some embodiments, recordation of the lift usage data is based on receipt of the signal and the additional signal and identification of the lift usage timing.

In some embodiments, a determination of whether a lift qualification threshold is met is based on receipt of the signal and the identification of the lift usage timing. The recording of the lift usage data may then include recording an occurrence of a lift when a determination is made that the lift qualification threshold is met.

Total lift usage timing during a time period may be identified for a electro-mechanical patient lifts at block 910 based on lift usage data for the electro-mechanical patient lifts.

A comparison of total lift usage timing to a compliance value may be made at block 912.

The compliance value may be modified at block 914 based on a result of comparison between the total lift usage timing and the compliance value.

The baseline data may be updated at block 1016 based on the number of patient lifts performed during the time period.

Figure 10:
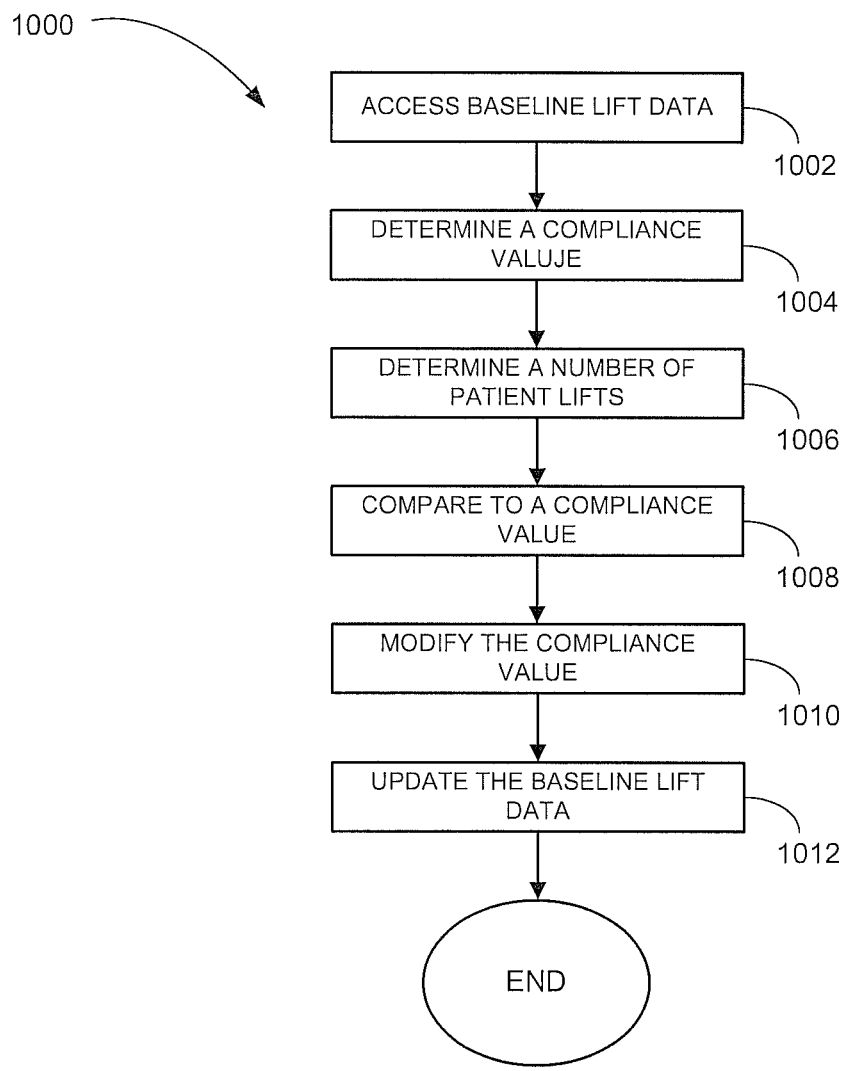

FIG. 10 illustrates a method 1000 for lift monitoring according to an example embodiment. The method 1000 may be performed by the monitoring computing device 106, the transmitter 110 of the system 100 (see FIG. 1), or may be otherwise performed.

Baseline lift data of a patient facility may be accessed at block 1002. The baseline lift data is associated with the electro-mechanical patient lifts in a patient facility. In some embodiments, the baseline lift data is accessed from the database 116. In other embodiments, the baseline lift data is received through a user interface.

A compliance value may be determined at block 1004 based on the baseline lift data. In some embodiments, the compliance value is associated with a targeted number of patient lift tasks to be performed in the area. In some embodiments, the compliance value may be associated with multiple lift types to be performed. In some embodiments, the compliance value is a compliance percentage. For example, the compliance value may be a percentage of a predetermined number of expected patient lifts.

The area may be the entire patient facility, a portion of the patient facility. The area may include a number of rooms of the patient facility.

A number of patient lifts performed during a time period in an area of a patient facility is determined at block 1006. The patient facility includes electro-mechanical patient lifts.

In some embodiments, the determination of the number of patient lifts performed is based on the baseline lift data and recorded lift usage data from at least a portion of the electro-mechanical patient lifts.

A comparison of the number of patient lifts performed to a compliance value may be made at block 1008.

At block 1010, modification of the compliance value is made based on a result of comparison between the number of patient lifts performed to the compliance value. The modification may include increasing or decreasing the compliance value. For example, if the number of patient lifts performed is greater than the compliance value, then the compliance value may be incrementally increased.

In some embodiments, a compliance adjustment may be received from a user and modification to the compliance value may be made based on the result of a comparison between the number of patient lifts performed to the compliance value and receipt of the compliance adjustment.

Figure 11:
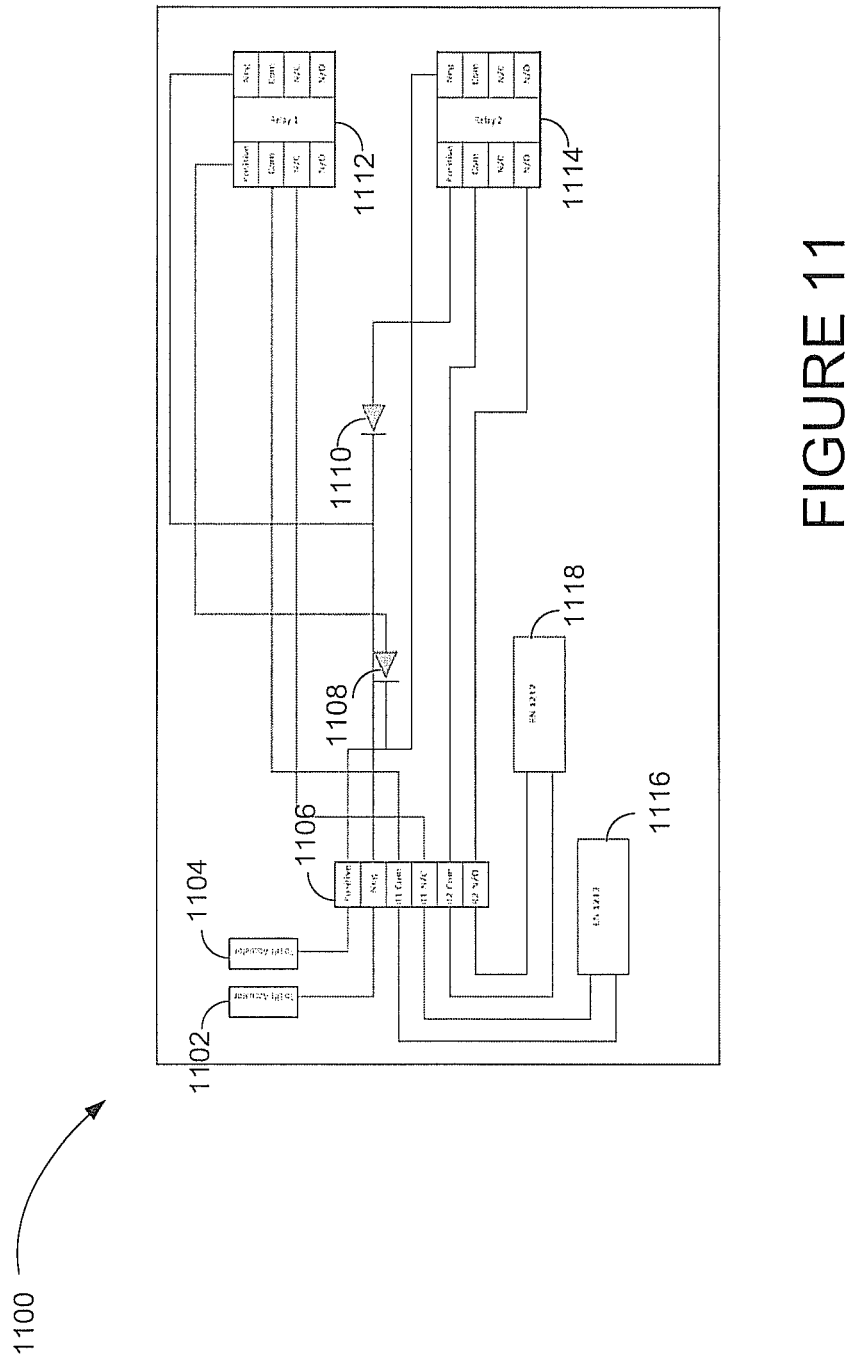
FIGS. 11 and 12 are diagrams of example measurement device configurations, according to example embodiments.

FIG. 11 is a diagram of an example measurement device configuration 1100, according to an example embodiment. The measurement device configuration 1100 may be used with the system 100 (see FIG. 1), or may be otherwise used.

The measurement device configuration 1100 includes connectors 1102, 1104 that are coupled to the electro-mechanical patient lift 102 (see FIG. 1). The connectors 1102, 1104 may be connected to actuators of the electro-mechanical patient lift 102, or may be otherwise coupled. The information (e.g., an amount of voltage) obtained from the electro-mechanical patient lift 102 by the connectors 1102, 1104 and is passed through a terminal strip 1106 and diodes 1108, 1110.

The information provided by the connectors 1102, 1104, is then received by relays 1112, 1114 and used by the relays 1112, 1114 to make a reading.

As shown, the connectors 1102, 1104, are coupled to positive and negative terminals of the terminal strip 1106. The negative terminal of the terminal strip 1106 is coupled to the negative terminal of a relay 1112 and through a diode 1110 to the negative terminal of a relay 1114. The positive terminal of the terminal strip 1106 is coupled through a diode 1108 to a positive terminal of the relay 1112 and to the positive terminal of the relay 1114.

The readings made by the relays 1112, 1114 are then passed through the terminal strip 1106 to transmitters 1116, 1118. The transmitters 1116, 1118 may be two separate transmitters, or may be two separate inputs on a single transmitter.

As shown, a com terminal of the relay 1112 is coupled to a transmitter 1116 through a R1 comm terminal of the terminal strip 1106. A normally closed terminal of the relay 1112 is coupled to the transmitter 1116 through a R1 normally closed terminal of the terminal strip 1116. A com terminal of the relay 1114 is coupled to a transmitter 1118 through a R2 comm terminal of the terminal strip 1106. A normally opened terminal of the relay 1114 is coupled to the transmitter 1118 through a R2 normally opened terminal of the terminal strip 1116.

Other embodiments of the measurement device configuration 1100 may include different components, different configurations, and/or different couplings.

Figure 12:
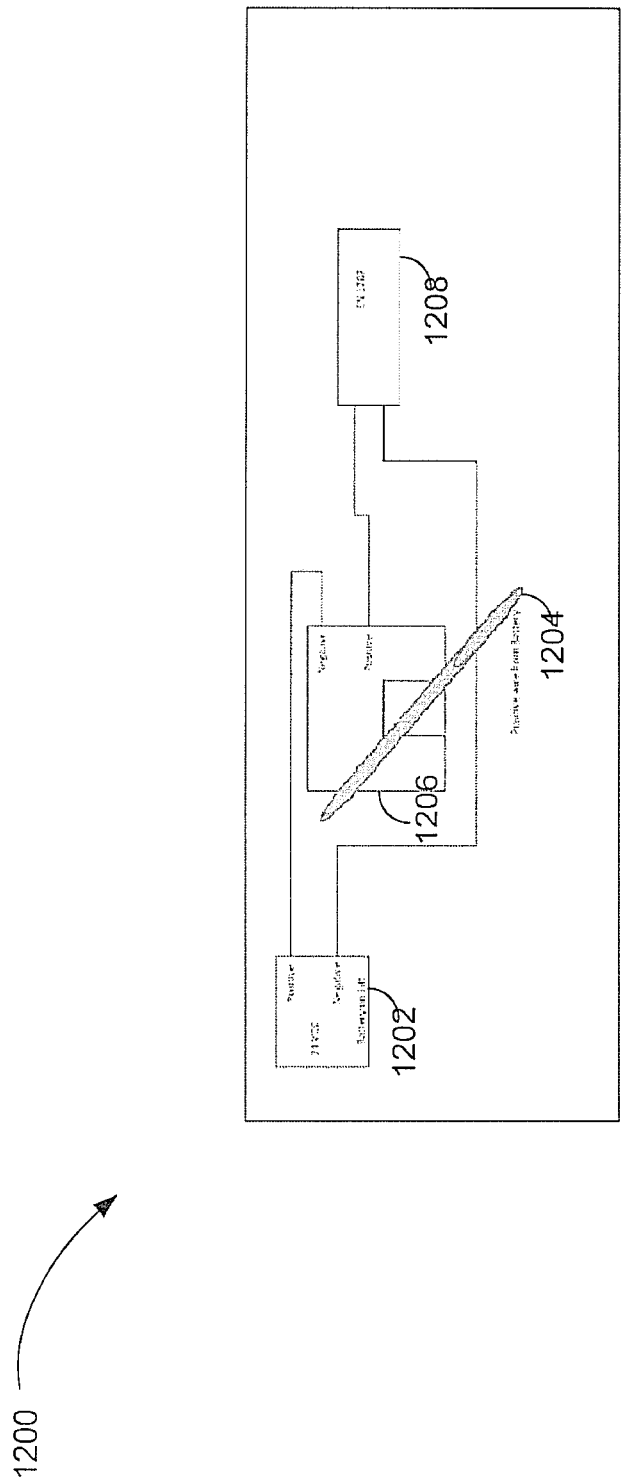

FIG. 12 is a diagram of an example measurement device configuration 1200, according to example embodiment. The measurement device configuration 1200 may be used with the system 100 (see FIG. 1), or may be otherwise used.

The measurement device configuration 1200 includes a battery 1202 of the electro-mechanical patient lift 102 (see FIG. 1) coupled to a current sensor 1206. As shown, the current sensor 1204 is wrapped around a positive wire 1206 of the battery 1202. The reading made by the current sensor 1204 is then provided to the transmitter 1206.

Other embodiments of the measurement device configuration 1200 may include different components, different configurations, and/or different couplings.

Figure 13:
FIGS. 13-19 are diagrams of example screenshots, according to example embodiments.

FIG. 13 is an example display 1300 of a screenshot, according to an example embodiment. In some embodiments, the display 1300 may be generated for a user interface to be displayed to the administrator of the system 100.

The display 1300 may allow the administrator to add patient lift equipment to be monitored by the monitoring computing device 106 of the monitoring system 130.

The display 1300 includes drop down menus for selecting the type of equipment to be monitored, forms for inputting specific equipment data, among others. Additionally, the display 1300 includes fields 1302, 1304, and 1306 for values that a patient facility could use as a basis for determining if a lift or task has been performed. For example, as shown in the display 1300, four seconds "Minimum Down" and four seconds "Minimum up" with an interval of twenty seconds between each "Minimum Down" and "Minimum Up" would constitute the completion of a lift or a task. The display 1300 may also include a field for the compliance set point (CSP) or compliance value for both day and night shifts.

The display 1400 may include a selection for identification of the manufacturer of the lift (e.g., Liko or Other Manufacture). The associated model numbers are also available for selection. The serial number for the electro-mechanical patient lift 102, the room or unit to which the electro-mechanical patient lift 102 is assigned, and a module identification associated with a serial number of the measuring device 106 may be identified. If the manufacture or model is unknown, the administrator may select overhead, sit-to stand and total lift.

The basis upon which the facility wants to use to determine if a task/lift has been performed may also be selected. For instance, the administrator may define that a task/lift occurs with at least four seconds up movement and four seconds of down movement. Global settings for a unit/department of the facility may be selected, or each particular electro-mechanical patient lift may have its own lift criteria. The administrator may also pick the interval between the first and the latter movement. For instance, if the electro-mechanical patient lift goes up or down for four seconds but then the interval time expires, the lift or task may not be recorded. Also, in the display may allow selection of how much time the lift is unused before lift data is stored or someone is notified regarding the activity.

Figure 14:

FIG. 14 is an example display 1400 of a screenshot, according to an example embodiment. In some embodiments, the display 1400 may be generated for a user interface to be displayed to the administrator of the system 100.

The display 1400 may present the type of equipment that is being monitored by the monitoring computing device 106 of the monitoring system 100. The display 1400 includes a listing of the equipment being monitored by the monitoring system 100 and the values used to determine whether a patient lift or task has occurred.

Figure 15:
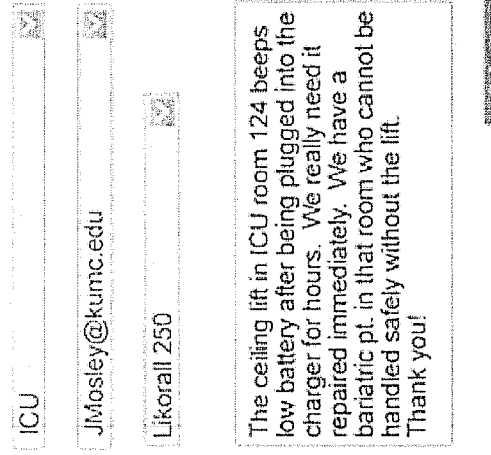
Figure 15:

FIG. 15 is an example display 1500 of a screenshot, according to an example embodiment. In some embodiments, the display 1500 may be generated for a user interface to be displayed to the administrator of the system 100.

In general, the display 1500 may be used to submit a repair request regarding the electronic mechanical patient lift 102. The repair request may specify the unit in which the electronic mechanical patient lift 102 is located, the administrator submitting the repair request, the type of the electronic mechanical patient lift 102, and comments provided by the administrator.

Figure 16:
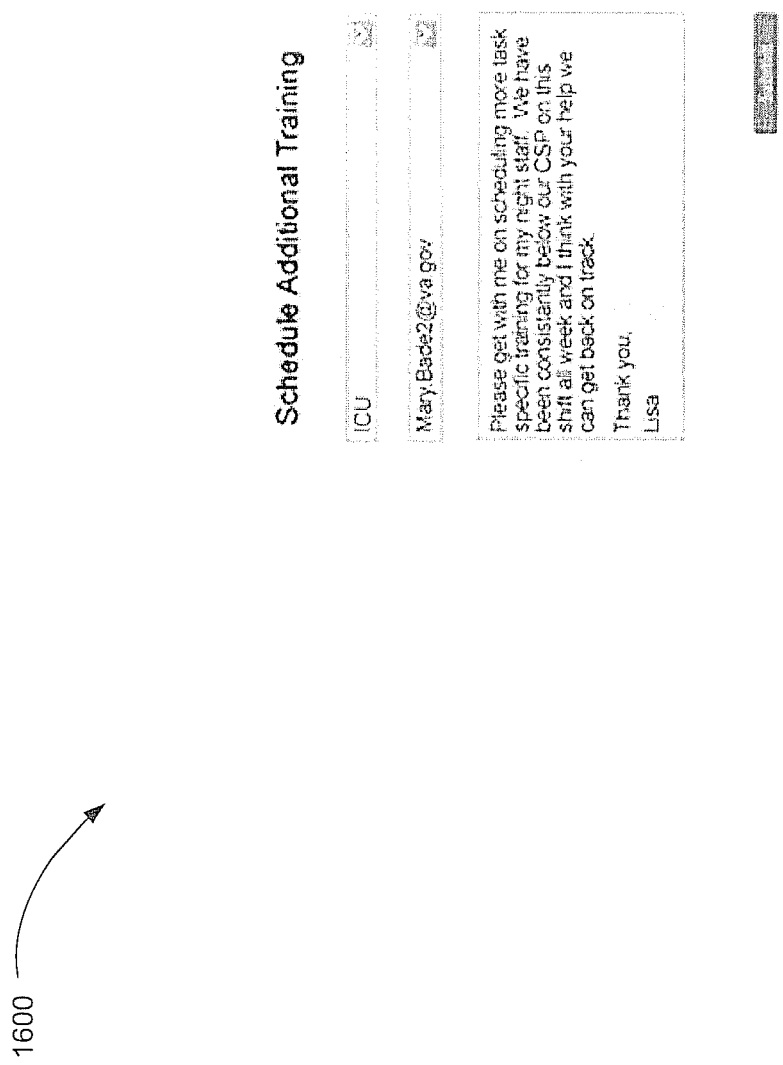

FIG. 16 is an example display 1600 of a screenshot, according to an example embodiment. In some embodiments, the display 1600 may be generated for a user interface to be displayed to the administrator of the system 100.

In general, the display 1600 may be used to submit a training request. The training request may specify the unit in which the electronic mechanical patient lift 102 is located, the administrator submitting the repair request, and comments provided by the administrator. In some embodiments, the training request may be generated for display based on low achievement with a compliance set point.

Figure 17:
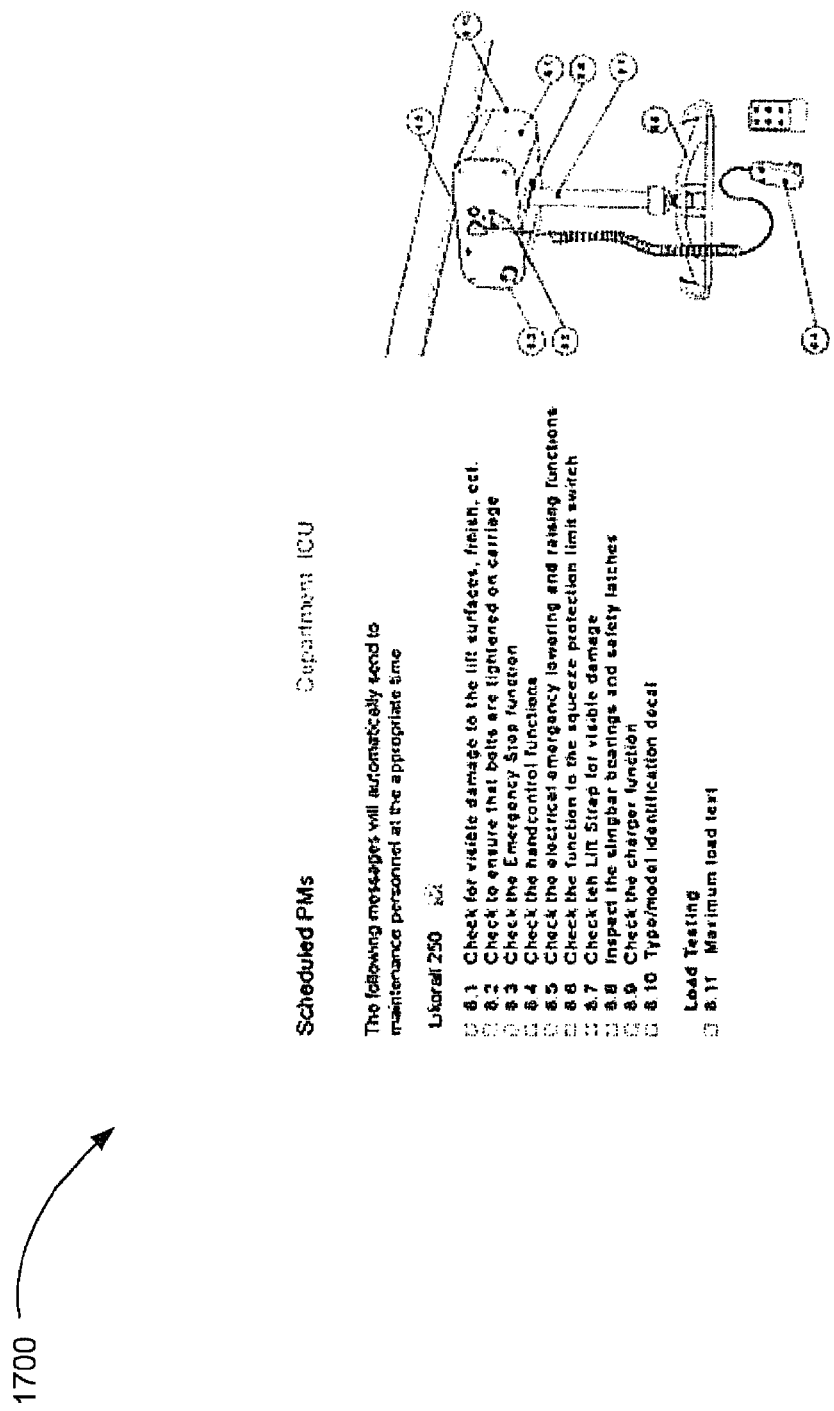

FIG. 17 is an example display 1700 of a screenshot, according to an example embodiment. In some embodiments, the display 1700 may be generated for a user interface to be displayed to the administrator of the system 100.

In general, the display 1700 may be used to automatically transmit a maintenance request to maintenance personnel regarding the use of a ceiling electronic mechanical patient lift 102. In some embodiments, the maintenance request may be generated for display and transmitted based usage of the electronic mechanical patient lift 102. The usage may be low usage, no usage, or usage for only particular types of lifts.

Figure 18:
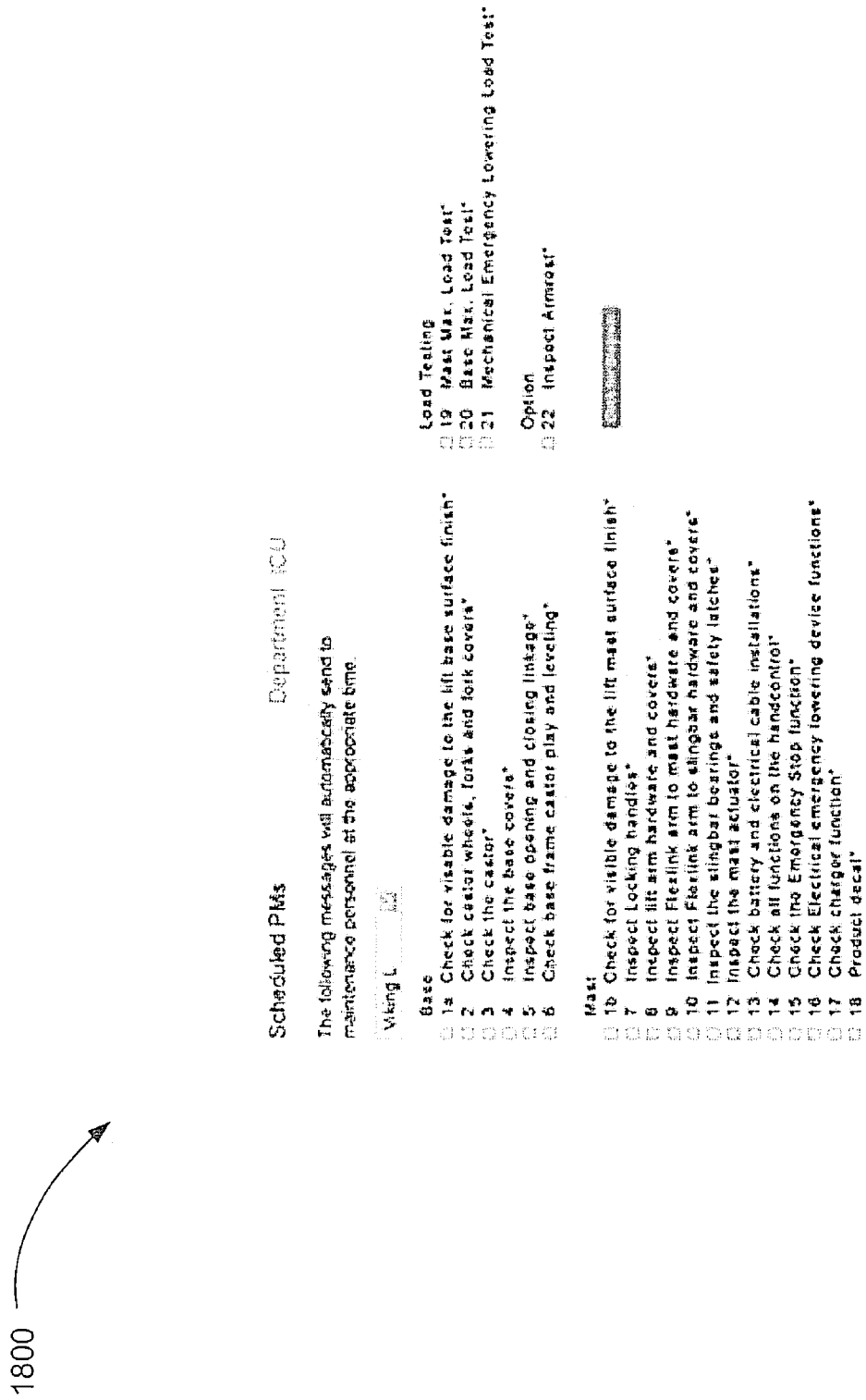

FIG. 18 is an example display 1800 of a screenshot, according to an example embodiment. In general, the display 1800 may be used to automatically transmit a maintenance request to maintenance personnel regarding the use of a mobile electronic mechanical patient lift 102. In some embodiments, the maintenance request may be generated for display and transmitted based usage of the electronic mechanical patient lift 102. The usage may be low usage, no usage, or usage for only particular types of lifts.

Figure 19:

FIG. 19 is an example display 1900 of a screenshot, according to an example embodiment. In some embodiments, the display 1900 may be generated for a user interface to be displayed to the administrator of the system 100.

In general, the display 1900 may be used to request additional information from the administrator regarding usage below a compliance set point. As shown in the display 1900, information regarding the rooms, the area, and the reason for being below the compliance set point may be identified.

In some embodiments, the displays 1900, 2000 may be used to initiate preventative maintenance for the electro-mechanical patient lift 102. The displays may then be transmitted (e.g., via email) to the appropriate department.

In some embodiments, the displays 1900, 2000 or other displays may include an electronic manual for the electro-mechanical patient lift 102.

Figure 20:
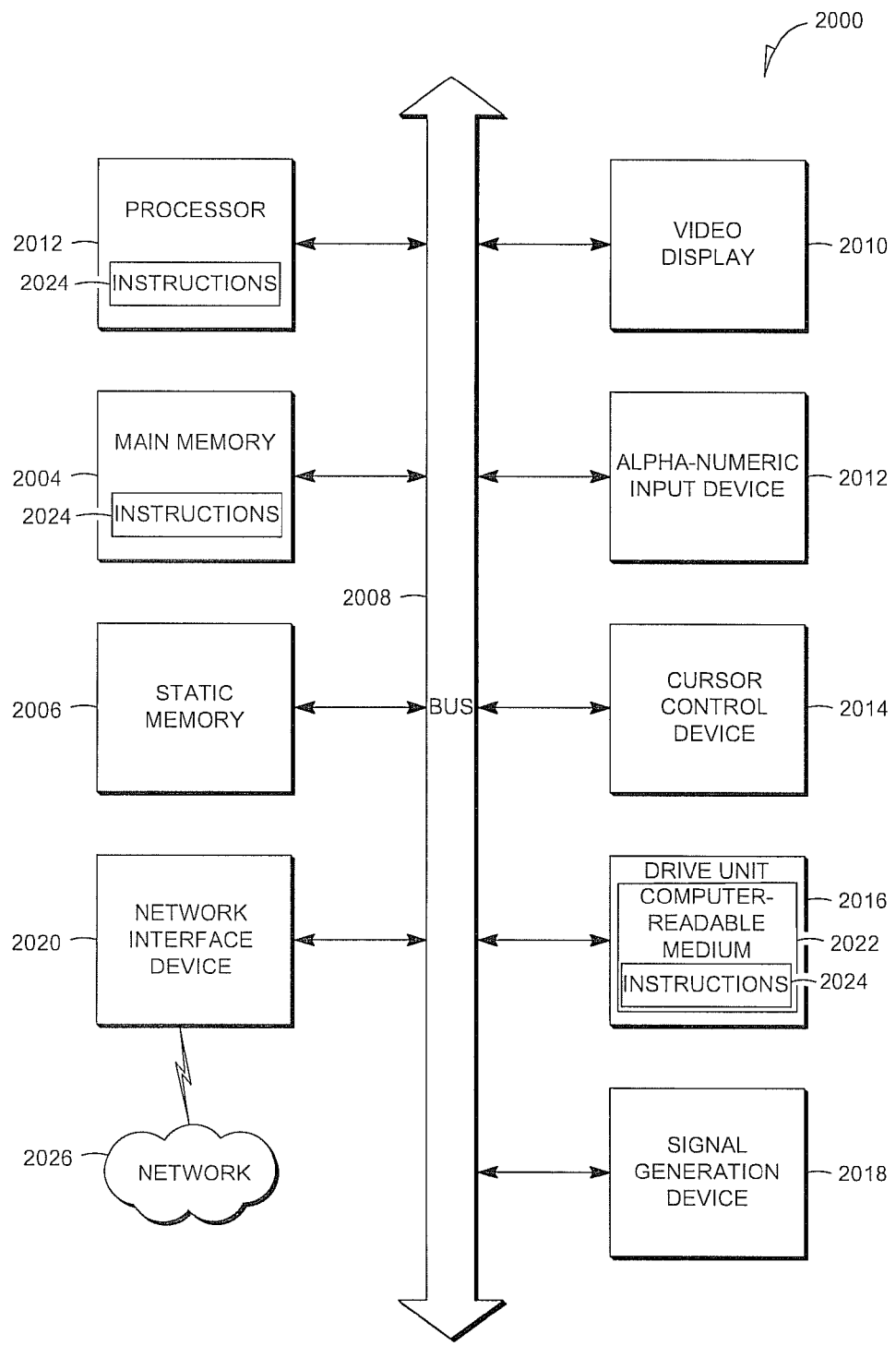
FIG. 20 is a block diagram of a machine in the example form of a computer system within which a set of instructions for causing the machine to perform any one or more of the methodologies discussed herein may be executed.

FIG. 20 shows a block diagram of a machine in the example form of a computer system 2000 within which a set of instructions may be executed causing the machine to perform any one or more of the methods, processes, operations, or methodologies discussed herein. The monitoring computing device 106, the transmitter 110, and/or the administrator device 118 may include the functionality of the one or more computer systems 2000.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 2000 includes a processor 2012 (e.g., a central processing unit (CPU) a graphics processing unit (GPU) or both), a main memory 2004 and a static memory 2006, which communicate with each other via a bus 2008. The computer system 2000 may further include a video display unit 1200 (e.g., a liquid crystal display (LCD) or a cathode ray tube (CRT)). The computer system 2000 also includes an alphanumeric input device 2012 (e.g., a keyboard), a cursor control device 2014 (e.g., a mouse), a drive unit 2016, a signal generation device 2018 (e.g., a speaker) and a network interface device 2020.

The drive unit 2016 includes a machine-readable medium 2022 on which is stored one or more sets of instructions (e.g., software 2024) embodying any one or more of the methodologies or functions described herein. The software 2024 may also reside, completely or at least partially, within the main memory 2004 and/or within the processor 2012 during execution thereof by the computer system 2000, the main memory 2004 and the processor 2012 also constituting machine-readable media.

The software 2024 may further be transmitted or received over a network 2026 via the network interface device 2020.

While the machine-readable medium 2022 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing or encoding a set of instructions for execution by the machine and that cause the machine to perform any one or more of the methodologies of the present invention. The term "machine-readable medium" shall accordingly be taken to include, but not be limited to, solid-state memories, and optical media, and magnetic media. In one embodiment, the machine-readable medium is a non-transitory machine-readable medium.

Certain systems, apparatus, applications or processes are described herein as including a number of modules. A module may be a unit of distinct functionality that may be presented in software, hardware, or combinations thereof. When the functionality of a module is performed in any part through software, the module includes a machine-readable medium. The modules may be regarded as being communicatively coupled.

The inventive subject matter may be represented in a variety of different embodiments of which there are many possible permutations.

In an example embodiment, a first operation signal may be received from a first relay coupled to an electro-mechanical patient lift when the electro-mechanical patient lift is being operated in a first position. A second operation signal may be received from a second relay coupled to the electro-mechanical patient lift when the electro-mechanical patient lift is being operated in a second position. A determination of whether a lift qualification threshold is met based on receiving the first operation signal and the second operation signal may be made. An occurrence of a lift may be recorded when a determination is made that the lift qualification threshold is met.

In an example embodiment, a measurement of current may be received from a current sensor coupled to an electro-mechanical patient lift. A determination of whether a lift qualification threshold is met based on receipt of the measurement of current. An occurrence of a lift may be recorded when a determination is made that the lift qualification threshold is met.

In an example embodiment, a wireless transmitter may be coupled to an electro-mechanical patient lift. A first relay and a second relay may be coupled to the wireless transmitter and the electro-mechanical patient lift. The first relay may activate when the electro-mechanical patient lift is being used in an up position and the second relay activates when the electro-mechanical patient lift is being used in a down position. The wireless transmitter may detect activation of the first relay and the second relay. The information regarding the activation of the first relay and the second relay may be sent to a monitoring computer device.

In an example embodiment, a wireless transmitter may be coupled to an electro-mechanical patient lift. A current sensor may be coupled to the wireless transmitter and the electro-mechanical patient lift. The current sensor may receive a measurement of current change from a current sensor coupled to a battery of the electro-mechanical patient lift and may provide the measurement to the wireless transmitter. The wireless transmitter may receive the measurement and transmit information including the measurement to a monitoring computer device.

In an example embodiment, an operation signal receiver module may receive a first operation signal from a first relay coupled to an electro-mechanical patient lift when the electro-mechanical patient lift is being operated in a first position and to receive a second operation signal from a second relay coupled to the electro-mechanical patient lift when the electro-mechanical patient lift is being operated in a second position. A lift qualification module may determine whether a lift qualification threshold is met based on the receiving of the first operation signal and the second operation signal. A recordation module may record an occurrence of a lift when a determination is made that the lift qualification threshold is met.

In an example embodiment, a measurement receiver module may receive a measurement of current from a current sensor coupled to an electro-mechanical patient lift. A lift qualification module may determine whether a lift qualification threshold is met based on the receiving of the measurement of current. A recordation module may record an occurrence of a lift when a determination is made that the lift qualification threshold is met.

In an example embodiment, a determination of a number of patient lifts performed during a time period in an area of a patient facility may be made. The patient facility may include a plurality of electro-mechanical patient lifts. A comparison the number of patient lifts performed to a compliance value may be performed. The compliance value may be modified based on a result of comparison between the number of patient lifts performed to the compliance value. The baseline data may be updated based on the number of patient lifts performed during the time period.

In an example embodiment, a signal may be received from a measuring device coupled to an electro-mechanical patient lift. Lift usage timing may be identified based on receipt of the signal. Lift usage data may be record based on receipt of the signal and identification of the lift usage timing.

Thus, methods and systems for lift monitoring have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving a first operation signal from a first relay coupled to an electro-mechanical patient lift when the electro-mechanical patient lift is being operated in a first position;
receiving a second operation signal from a second relay coupled to the electro-mechanical patient lift when the electro-mechanical patient lift is being operated in a second position;
determining whether a lift qualification threshold is met based on receipt of the first operation signal and the second operation signal;
recording an occurrence of a lift when a determination is made that the lift qualification threshold is met
measuring a first signal duration of the receiving of the first operation signal; and
measuring a second signal duration of the receiving of the second operation signal,
wherein the determining of whether the lift qualification threshold includes determining whether the first signal duration meets an up time threshold and determining whether the second signal duration meets a down time threshold.

2. The method of claim 1, further comprising:
receiving a transmitter identifier from a transmitter when the electro-mechanical patient lift is being operated, the transmitter associated with the first relay and the second relay; and
recording the transmitter identifier with the occurrence of the lift when the determination is made that the lift qualification threshold is met.

3. The method of claim 1, further comprising:
receiving a transmitter identifier from a transmitter when the electro-mechanical patient lift is being operated, the transmitter associated with the first relay and the second relay;
identifying a location associated with the transmitter identifier; and
recording the location with the occurrence of the lift when the determination is made that the lift qualification threshold is met.

4. The method of claim 1, further comprising:
receiving positional data associated with a location of the electro-mechanical patient lift; and
recording the location with the occurrence of the lift when the determination is made that the lift qualification threshold is met.

5. The method of claim 1, further comprising:
recording an occurrence of a non-lift when a determination is made that the lift qualification threshold is not met.

6. The method of claim 1, wherein the lift qualification threshold includes an up time threshold and a down time threshold.

7. The method of claim 6, further comprising:
receiving a designation of the up time threshold and the down time threshold,
wherein the determining of whether the lift qualification is met is based on the receiving of the first operation signal, the second operation signal, and the designation of the up time threshold and the down time threshold.

8. The method of claim 1, further comprising:
receiving a load measurement from a load sensor coupled to the electro-mechanical patient lift; and
determining whether the load measurement meets a load threshold,
wherein the determining of whether the lift qualification threshold is met based on the receiving of the first operation signal and the second operation signal and a determination that the load measurement meets the load threshold.

9. The method of claim 1, wherein the first position is an up position and the second position is a down position.

10. A system comprising:
a wireless transmitter coupled to an electro-mechanical patient lift; and
a first relay and a second relay coupled to the wireless transmitter and the electro-mechanical patient lift,
wherein the first relay activates when the electro-mechanical patient lift is being used in an up position and the second relay activates when the electro-mechanical patient lift is being used in a down position, and the wireless transmitter to detect activation of the first relay and the second relay and transmit information regarding the activation of the first relay and the second relay to a monitoring computer device, and
a process executed by the monitoring computer comprising:
receiving a first operation signal from the first relay coupled to the electro-mechanical patient lift when the electro-mechanical patient lift is being operated in the up position;
receiving a second operation signal from the second relay coupled to the electro-mechanical patient lift when the electro-mechanical patient lift is being operated in the down position;
determining whether a lift qualification threshold is met based on receipt of the first operation signal and the second operation signal;

recording an occurrence of a lift when a determination is made that the lift qualification threshold is met;
measuring a first signal duration of the receiving of the first operation signal; and
measuring a second signal duration of the receiving of the second operation signal,
wherein the determining of whether the lift qualification threshold includes determining whether the first signal duration meets an up time threshold and determining whether the second signal duration meets a down time threshold.

11. The system of claim 10, further comprising:
the electro-mechanical patient lift, wherein the first relay and the second relay are integrated into the electro-mechanical patient lift.

12. The system of claim 10, further comprising:
the monitoring computer device to receive the information regarding the activation of the first relay and the second relay, determine whether a lift qualification threshold has been met based on the receiving of the information, and record a lift when a determination is made that the lift qualification has been met.

13. The system of claim 10, wherein the information further includes a transmitter identifier of the wireless transmitter coupled to the electro-mechanical patient lift.

14. The system of claim 13, wherein the transmitter identifier includes at least one of a serial number of the electro-mechanical patient lift, a room number associated with electro-mechanical patient lift, a unit associated with electro-mechanical patient lift, a department associated with electro-mechanical patient lift, or combinations thereof.

15. A machine-readable medium comprising instructions, which when executed by one or more processors, cause the one or more processors to perform the following operations:
receive a first operation signal from a first relay coupled to an electro-mechanical patient lift when the electro-mechanical patient lift is being operated in a first position;
receive a second operation signal from a second relay coupled to the electro-mechanical patient lift when the electro-mechanical patient lift is being operated in a second position;
determine whether a lift qualification threshold is met based on the receiving of the first operation signal and the second operation signal;
record an occurrence of a lift when a determination is made that the lift qualification threshold is met;
wherein determining whether the lift qualification has been met comprises:
measuring a first signal duration of the receiving of the first operation signal; and
measuring a second signal duration of the receiving of the second operation signal,
wherein the determining of whether the lift qualification threshold includes determining whether the first signal duration meets an up time threshold and determining whether the second signal duration meets a down time threshold.

16. A machine-readable medium comprising instructions, which when executed by one or more processors, cause the one or more processors to perform the following operations:
receive a measurement of current from a current sensor coupled to an electro-mechanical patient lift;
determine whether a lift qualification threshold is met based on the receiving of the measurement of current; and
record an occurrence of a lift when a determination is made that the lift qualification threshold is met, wherein determining whether the lift qualification threshold is met further comprises:
measuring a first signal duration of the receiving of the measurement of current; and
measuring a second signal duration of the receiving of the measurement of current,
wherein the determining of whether the lift qualification threshold includes determining whether the first signal duration meets a up time threshold and determining whether the second signal duration meets a down time threshold.

* * * * *